(12) United States Patent
Lally

(10) Patent No.: US 6,533,821 B1
(45) Date of Patent: Mar. 18, 2003

(54) BIO-ADHESIVE COMPOSITION, METHOD FOR ADHERING OBJECTS TO BONE

(76) Inventor: Thomas Lally, 603 Mallard La., Oak Brook, IL (US) 60423

( * ) Notice: Subject to any disclaimer, the term of this patent is extended or adjusted under 35 U.S.C. 154(b) by 4 days.

(21) Appl. No.: 09/602,067

(22) Filed: Jun. 22, 2000

(51) Int. Cl.$^7$ .................................................. A61F 2/36

(52) U.S. Cl. ................. 623/23.62; 623/23.51; 424/426; 523/116

(58) Field of Search ............................ 623/23.51, 23.6, 623/23.61, 23.62, 23.63; 106/690; 433/172, 180; 523/116; 424/426

(56) References Cited

U.S. PATENT DOCUMENTS

| | | | | |
|---|---|---|---|---|
| 5,262,166 A | * | 11/1993 | Liu et al. | 106/35 |
| 6,204,214 B1 | * | 3/2001 | Singh et al. | 106/690 |
| 6,224,635 B1 | * | 5/2001 | Ricci et al. | 623/23.62 |
| 6,306,925 B1 | * | 10/2001 | Clupper et al. | 523/113 |

* cited by examiner

Primary Examiner—Corrine McDermott
Assistant Examiner—Urmi Chattopadhyay
(74) Attorney, Agent, or Firm—Cherskov & Flaynik

(57) ABSTRACT

The invention provides for a bio-adhesive derived from a mixture comprising $KH_2PO_4$, a metal oxide, a calcium-containing compound, and water. Also provided is a reabsorbable bone substitute derived from a mixture comprising $KH_2PO_4$ and an oxide in a 1:1 weight percent ratio, a calcium-containing compound, and water.

7 Claims, 2 Drawing Sheets

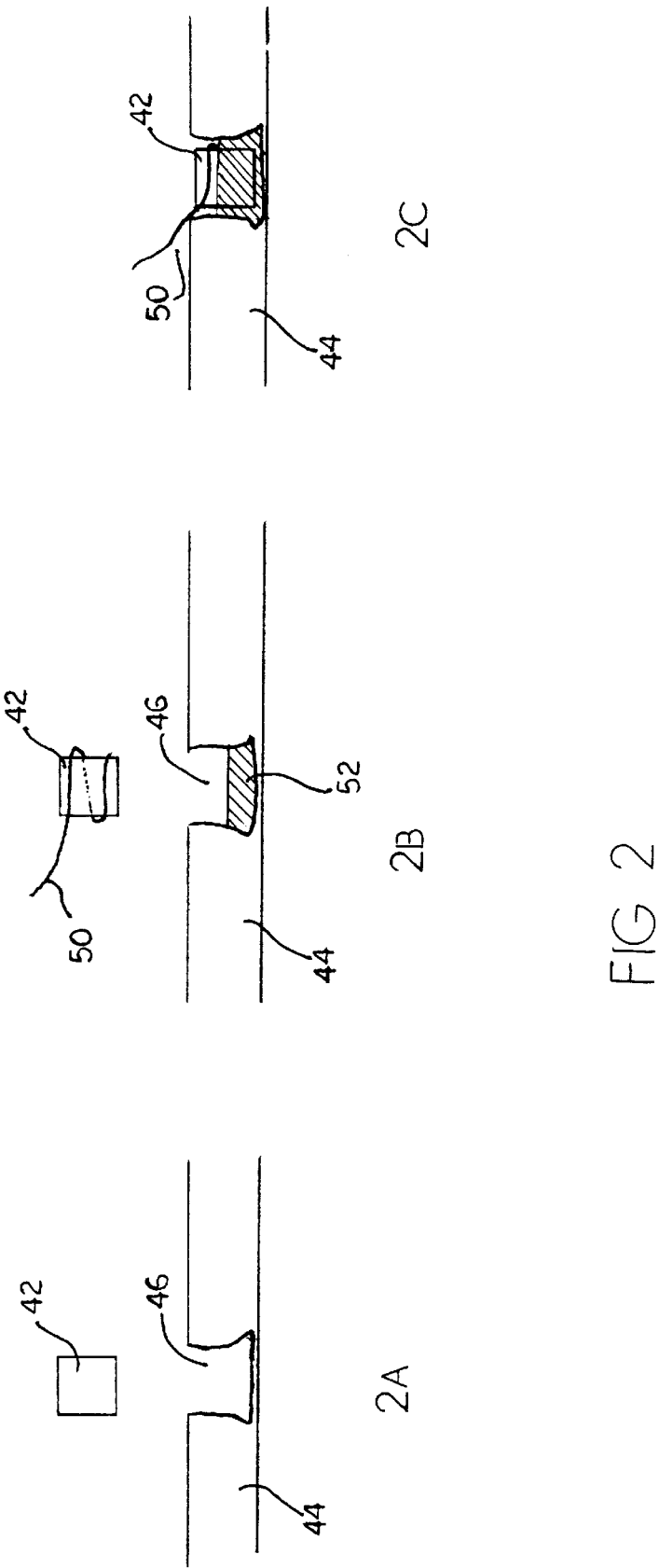

BIO-ADHESIVE COMPOSITION, METHOD FOR ADHERING OBJECTS TO BONE

BACKGROUND OF THE INVENTION

1. Field of the Invention

This invention relates to a bio-adhesive composition and more specifically, this invention relates to a phosphate-based adhesive for bone, ligament and tendon repair and stabilization, and a method for applying the composition during surgery.

2. Background of the Invention

The use of synthetic materials to expedite healing is becoming more widespread. A burgeoning area of growth is the use of relatively inert hardening agents for use as bone substitute materials. In such uses, surgeons apply the substitute material to fractures. In situ hardening of the material occurs either during surgery, or after suturing.

Synthetic hardening agents include polymethylmethacrylate and other similar polymers. Alternatively, a myriad of calcium-containing substances are utilized as bone substitutes. For example, U.S. Pat. No. 5,605,713 issued to Boltong on Feb. 25, 1997, and U.S. Pat. No. 5,152,836 issued to Hirano on Oct. 6, 1992 discloses the use of calcium orthophosphate cements as a bone substitute.

However, these and other disclosures appear to provide a material merely for filling bone defects. None of the currently available materials provide both an adhesive filler and a bio-adhesive, to both fill voids and fractures and also provide structural support to the bone, and adjacent structures such as ligaments and tendons. Also, some of these compounds have high molar ratios of Ca to P, and therefore tend to remain in the body and are not resorbed.

None of the known biocomposites or biopolymers provide a means for enhancing adhesion to bone and existing structures aside from the chemical adhering aspects of the mixture. As such, fasteners (such as screws or clamps) often are utilized to hold the physiological structures until the mixtures can cure. Often these fasteners are not biodegradable.

A need exists in the art for a reabsorbable bio-adhesive. The adhesive should incorporate typical calcium-containing moieties to minimize its cost. The adhesive should maintain its workability and ultimately "set" under physiologic conditions, including temperature, pH and humidity. The material should be absorbed by the body without any untoward side effects. Also, the adhesive should be applicable to bone, ligaments and tendons so as to provide both void-filling and fracture repair capabilities and structural support. Finally, the bioadhesive should confer means to both chemically and mechanically fasten structures in place in vivo.

SUMMARY OF THE INVENTION

An object of the present invention is to provide a substance and a method for a bio-adhesive that overcomes many of the disadvantages of the prior art.

Another object of the present invention is to provide a bio-adhesive to effect the in-situ repair and adherence of body parts to each other and to adjacent structures. A feature of the invention is that the adhesive "sets" at physiologic temperatures, and pH and within approximately 10 and 15 minutes. Another feature of the invention is that the bio-adhesive expands in vivo. An advantage of the invented formulation is its ability to simultaneously fill bone defects and provide structural support. Another advantage is that the expandability of the adhesive during setting or curing confers additional mechanical contact between the adhesive and body parts and between body parts and such adjacent structures as manmade materials and biological materials.

Yet another object of the present invention is to provide a bone substitute and a platform for bone formation. A feature of the invention is the utilization of $CaSiO_3$ or $Ca_{10}(PO_4)_6(OH)_2$ in combination with MgO and magnesium potassium phosphate to prepare the material. An advantage of the substance is its gradual absorption by the body without rejection or reaction to contacted structures.

Briefly, the invention provides a bio-adhesive comprising a means for attaching objects to bone; a means for enhancing said attachment means; and a means for facilitating in vivo degradation of the bio-adhesive. The bioadhesive is derived from a mixture comprising $KH_2PO_4$, a metal oxide, a calcium-containing compound, and water. One such compound is tricalcium phosphate.

Also provided is a method for fastening structures to bone surface, in vivo, the method comprising accessing the bone surface through a surgically-induced incision; simultaneously applying a phosphate-containing bio-adhesive to the structures and to the bone surface; closing the incision; and allowing the adhesive to expand.

BRIEF DESCRIPTION OF THE DRAWING

Other objects, features, and advantages of the present invention will become apparent from the following description and the accompanying drawings, wherein:

FIG. 2 is a schematic diagram depicting a method for attaching ligaments, tendons and other structures to bone utilizing the invented bioadhesive, in accordance with features of the present invention.

DETAILED DESCRIPTION OF THE INVENTION

Figure 1:
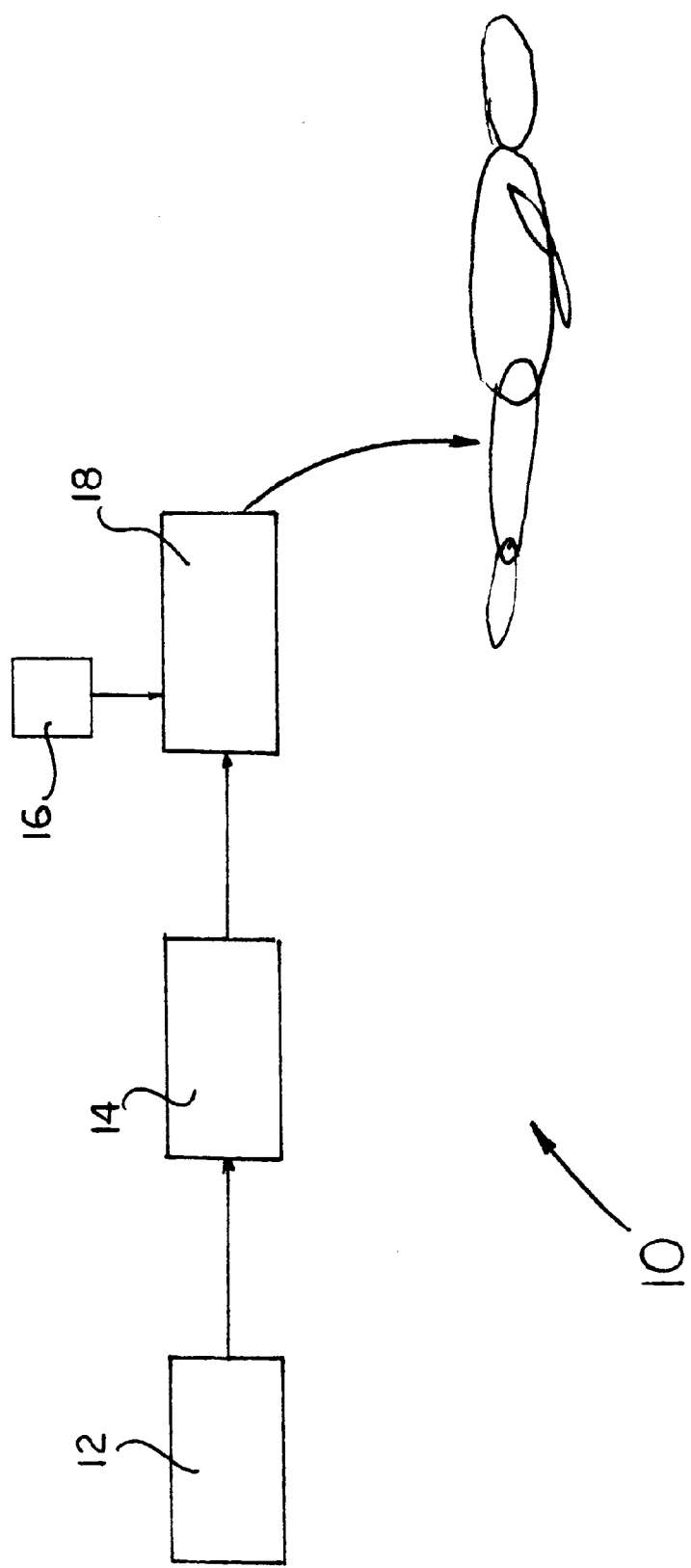
FIG. 1 is a schematic diagram depicting a method for producing the invented mixture, in accordance with features of the present invention.

The invention provides for a bio-adhesive for in-situ (i.e. in vivo) attachment of biological structures to each other and to manmade substrates. The bio-adhesive also facilitates the repair of bone, ligaments, tendons and adjacent structures. Also provided is a bone substitute for use in surgical repair. The invented formulation is usable at a myriad of temperatures, pH ranges, humidity levels and pressures. However, the formulation is designed to be utilized at all physiological temperatures, pH ranges, and fluid concentrations. The mixture typically is injectable, prior to setting, and exhibits neutral pH after setting. It is absorbed by the host over a period of time.

The mixture is particularly useful in situations (such as plastic surgery) whereby the use of metallic fasteners and other non-bioabsorbable materials are to be assiduously avoided. The material also is useful where a certain amount of expansion or swelling is to be expected after surgery, for example, in skull surgeries. It is a good platform for bone-formation.

Generally, the bio-adhesive and the bone substitute are derived from a hydrated mixture which comprises $KH_2PO_4$, a metal oxide, and a calcium containing compound. A preferred mixture is the following:

| | |
|---|---|
| $KH_2PO_4$ | 45 percent |
| MgO | 45 percent |
| Calcium-containing compound | 10 percent (whereby compound is either $CaSiO_3$ or $Ca_{10}(PO_4)_6(OH)_2$) |
| $H_2O$ | 25 percent by weight |

While the above formulation and weight percents are the most preferred proportions, a range of the constituents also can be utilized. For example, between 40 and 50 weight percent of the $KH_2PO_4$ can be utilized. Between 35 and 50 weight percent of the MgO also can be utilized. The ratio of $KH_2PO_4$ to the MgO should be between 1:0.5 and 1:1. As can be determined above, the ratio in the preferred mixture is 1:1.

Also, aside from MgO, a myriad of other oxide and hydroxide powders can be utilized, including, but not limited to FeO, $Al(OH)_3$, $Fe_2O_3$, $Fe_3O_4$ and $Zr(OH)_4$.

The inventors surmise that un-reacted magnesium is at least partly responsible for the in vivo expandability characteristics of the bio-adhesive. Specifically the magnesium oxide reacts with water and serum in and around the living tissue to yield $Mg(OH)_2$ and magnesium salts. It has been found that the material expands to between 0.15 and 0.20 percent of volume during curing in moisture.

Substance Preparation Detail

A schematic diagram of the mixture preparation is designated as numeral 10 in FIG. 1. Oxide powder is a salient ingredient in the invented mixture. Optionally, the oxide is subjected to a calcination process, 12. Calcination durations and temperatures are determined empirically, depending on the final characteristics and setting times desired. Generally, however, calcination temperatures of up to 1300° C. for up to several hours are typical. Generally, pharmaceutical grade oxides are utilized.

After calcination, the oxide powder is mixed with the potassium phosphate compound and the compound tricalcium phosphate until an homogenous dry-phase results 14. One method for sizing and homogenizing the various powders is via vibratory milling. Another homogenization method utilizes a ribbon mixer wherein the particles are ground to a fineness of approximately 20–30 microns.

Upon homogenization, wherein all of the constituents are contained in a dry homogenous mixture 14, water 16 is added up to 25 percent of the weight of the resulting slurry 18. The slurry is produced at the user site.

Bonding occurs primarily between the adhesive and bone. However, the adhesive also bonds to itself, or to soft tissue. The inventor has found that the use of phosphoric acid instead of water increases the bonding strength of the resulting material. The molarity of the phosphoric acid can vary, as long as the eventual pH of the slurry is not hazardous to the patient, or contraindicative to healing. Generally, a slurry pH of between 6 and 8 is appropriate.

Attachment Detail

FIG. 2 depicts a method designated as numeral 40, for utilizing the invented, bioadhesive to attach soft tissue to bone, in vivo and/or in situ. Generally, the method consists of first isolating a piece of bone 42 from a larger structure 44. The bone piece can be isolated by any convenient method, such as by surgical coring, or carving.

Upon removal of the piece of bone 42, the larger structure 44 will contain a region defining a cavity 46. The cavity is further adapted to simultaneously receive and contain the bone piece, adhesive and the soft tissue structure. Preferably, the cavity will define an annular space 48 along the cavity periphery.

In a second step of the method, depicted as 2B in FIG. 2, a ligament, tendon or other soft tissue structure 50 is wrapped around the bone piece 42. Also, bioadhesive 52 is placed in the cavity 46.

In a third step of the method, depicted as 2C in FIG. 2, the wrapped bone piece is placed into the cavity 46. While a certain amount of friction will keep the inserted piece from slipping out of the cavity, additional mechanical fastening is conferred by the expansive characteristics of the bioadhesive. Specifically, and as discussed supra, the bioadhesive will expand from between 0.1 and 0.3 volume percent, and more typically from 0.15 to 0.20 volume percent. This expansion results in a tighter fit of the piece into the cavity, but not so tight as to initiate necrosis of the bone or soft-tissue.

The annular region 48 discussed supra also results in a plug which will not fall out of the cavity inasmuch as the plug and the bioadhesive, the later of which migrates into the annular space, becomes integrally molded to together during the adhesive-curing process. By the time the bioadhesive is absorbed by the body, additional bone will have supplanted the bioadhesive so that the new bone is now integral with the larger bone 44 structure.

As a deviation from the above-discussed method, adhesive is not placed into the cavity. Rather, the adhesive is first placed on the bone piece 42 wrapped with the soft tissue structure, as depicted in FIG. 2B. Also, instead of an actual bone piece 42, a plug comprising solidified bioadhesive is used. The viability of inserting solidified, absorbable bioadhesive into bone is illustrated in Example 1, infra.

EXAMPLE 1

The above-disclosed material was tested in the laboratory for its bone-substitution properties. For the calcium-containing compound material, $Ca_{10}(PO_4)_6(OH)_2$ was utilized.

Generally, ASTM Protocol F763-87 (Reapproved 1993), incorporated herein by reference, was utilized. Eight Sprague-Dawley rats weighing approximately 375 grams were utilized in this example. Cylindrical rods of the experimental bone substitute were placed in the bone of the rats to determine the compatibility of the substitute to the rats' physiology. The experiment also was conducted to determine the utility of the composition, i.e., to determine how well the composition mimicked natural bone in weight-bearing scenarios.

Cylindrical rods of the bone substitute, measuring 1 cm long and 1.7 mm in diameter were made by injecting liquified bioadhesive into the lumens of 16 gauge IV catheters, then allowing the bioadhesive to harden to rods. The rods, removed from the catheter molds, were subsequently sterilized. A myriad of sterilization methods are suitable, including but not limited to, irradiation, autoclaving, or uv-light exposure. Dry autoclaving is a preferable autoclaving method.

Each rat was given an intramuscular injection of Cefazolin. Subsequently, and under a general anesthesia (Ketamine/Xylene) the distal left femoral articular surface was accessed through a medial parapetellar arthrotomy so that the intercondylar notch was identified.

A 1 cm long cavity was drilled with a 0.062 inch K-wire. A solid bone substitute plug was inserted in the cavity so that the distal end lay just below the level of the articular surface. The bone capsule and skin were closed separately with absorbable sutures. The rats were allowed to bear weight as tolerated.

Two rats were sacrificed at 3, 6, 9 and 12 weeks. Distal femurs and knee joints were harvested, and x-rays of the specimens were obtained. The specimens were then processed and embedded in methylmethacrylate. Histologic sections were made of the distal femur and the knee joint. Sections were reviewed under the light microscope for evidence of tissue reaction.

No postoperative systemic reactions occurred in the rats. No change in behavior was noted. All surgical wounds healed uneventfully. Histologic sections at different chronologic stages showed no tissue reaction towards the bone substitute in both the medullary canal and synovial cavity.

The invented substance gradually disintegrated without evidence of macrophage engulfment. X-rays showed gradual absorption of the substance without bone reaction.

At 115° F., a one-half inch by one-half inch cube of the substance has a compressive strength of approximately 55 MPa. The substance exhibits a flexural strength of approximately 28 MPa.

While the invention has been described with reference to details of the illustrated embodiment, these details are not intended to limit the scope of the invention as defined in the appended claims. For example, the adhesive has uses in all areas of orthopedics, plastic surgery (particularly where nonabsorbable mechanical fasteners are contraindicated), dentistry, neurosurgery, and veterinary science.

The inorganic bio-adhesive has been found to be non-toxic to cells and absorbable in situ. It rapidly attains strengths of more than 9000 pounds per square inch (psi). It sets in water, so as to be a suitable water hydraulic cement. The substance also can be instantly cured (i.e., hardened) by an outside heat source, such as, but not limited to, laser light.

An altered formulation of the bioadhesive has resulted in a moldable and castable material, thereby making it ideal as a refractory. One refractory formulation is comprised of magnesium potassium phosphate, magnesium oxide, and tricalcium phosphate. This refractory formulation can be adapted to prevent molten metal from sticking to it with the addition of microsilicas. A suitable microsilica is calcium silicate, in particle sizes ranging from approximately 10 microns to 40 microns.

Exemplary formulations of the refractory binder include the following:

Formulation I:

| | |
|---|---|
| Magnesium potassium phosphate (technical grade-30 microns) | 64%* |
| Magnesium oxide (technical grade) | 32% |
| Tricalcium Phosphate | 32% |

*Weight percent

The composition of Formulation I can be combined with a filler so that the ultimate mixture contains between 8 and 25 percent by weight of the formulation and 75 to 92 percent by weight of filler. The variation of binder percentage depends on desired consistency and use of the ultimate mixture.

Formulation II:

| | |
|---|---|
| Magnesium potassium phosphate (technical grade as above) | 61%* |
| Magnesium oxide (technical grade-calcined) | 31% |
| Tricalcium phosphate | 4% |
| CaSiO$_3$ | 4% |

*Weight percent

In Formulation II, CaSiO$_3$ is added to reduce build-up of slag when the binder is used in castable formulations. The silicate addition also reduces build-up in refractories which come in contact with molten metals.

Formulation III:

| | |
|---|---|
| Magnesium potassium phosphate | 45%* |
| Magnesium oxide | 45% |
| Tricalcium phosphate | 10% |

*Weight percent

Formulation III is suitable for casting refractory oven parts, panels, blocks and tiles. In such applications, binder is usually present at between 80 and 90 weight percent, with the remainder being filler.

Formulation IV

| | |
|---|---|
| Magnesium potassium phosphate | 41%* |
| Magnesium oxide | 41% |
| Tricalcium phosphate | 9% |
| Calcium silicate | 9% |

*Weight percent

Water is added to up to 25 weight percent of the formulation, and preferably 22 to 25 weight percent.

Formulation IV is a multi-purpose refractory grade ceramic cement which can also be used for bonding formed parts together, filling voids in finished castables, and for in vivo repair of fractures.

Formulation V

| | |
|---|---|
| Magnesium potassium phosphate | 41%* |
| Magnesium oxide | 41% |
| Tricalcium phosphate | 9% |
| Silicon dioxide | 9% |

*Weight Percent

Water is added up to 25 weight percent and preferably between 22 and 25 weight percent.

Formulation V is a dental cement suitable for casting of impressions and as a refractory mold for teeth, bridges and partials.

Some of the formulations disclosed herein incorporate fillers. Exemplary fillers include, but are not limited to, mullite, alumina, sand, clay, volcanic glasses, kyanite, bauxite, aluminum oxide, silicon oxide, chrome oxide, iron oxide and mixtures thereof.

As discussed supra in the materials preparation portion of the bio-adhesive formulation, components of the refractory mixture can be dry-mixed and homogenized via a myriad of devices. The material is shipped dry to the ultimate situs of usage and then applied as a slurry once water is added. The amount of water added depends on the workability desired. Generally, and unless additional heat is applied, the exothermic reaction resulting from the slurry formation results in the refractory curing in approximately three hours or less. Use of the refractory can occur within three hours after curing. If outside heat sources are used, for example lasers, the refractory cures within minutes.

The new refractory, with or without the addition of micro-silicates, results in a final green strength of approximately 8500 psi.

The embodiment of the invention in which an exclusive property or privilege is claimed is defined as follows:

1. A bio-adhesive comprising:
   a) means for attaching objects to bone;
   b) means for enhancing said attachment means; and
   c) means for facilitating in vivo degradation of the bio-adhesive,
      wherein said bio-adhesive is derived from a mixture of $KH_2PO_4$, metal oxide, a calcium compound, and water and the weight percent ratio of $KH_2PO_4$ and the oxide ranges from between approximately 1:0.5 and 1:1.

2. The bio-adhesive as recited in claim 1 wherein the objects are manmade materials selected from the group consisting of metal, composite, ceramic, and combinations thereof.

3. The bio-adhesive as recited in claim 1 wherein the objects are biological materials selected from the group consisting of ligaments, tendons, bone, teeth, and blood vessels.

4. The bio-adhesive as recited in claim 1 wherein the enhancement means is the ability of the bio-adhesive to expand in vivo during setting.

5. The bio-adhesive as recited in claim 1 wherein the oxide is calcinated.

6. The bio-adhesive as recited in claim 1 wherein the calcium compound is $Ca_{10}(PO_4)_6(OH)_2$.

7. A bio-adhesive comprising:
   a) means for attaching objects to bone;
   b) means for enhancing said attachment means; and
   c) means for facilitating in vivo degradation of the bio-adhesive,
      wherein said bio-adhesive is derived from a mixture of $KH_2PO_4$, metal oxide wherein the metal oxide is MgO, a calcium compound, and water and the weight percent ratio of $KH_2PO_4$ and MgO is 1:1.

* * * * *